United States Patent
Steinbrenner

(10) Patent No.: US 7,148,177 B2
(45) Date of Patent: Dec. 12, 2006

(54) METHOD FOR PRODUCING ALKALI METAL CATALYST AND USE THEREOF FOR THE SIDE-CHAIN ALKLATION OF ALKYL AROMATICS

(75) Inventor: Ulrich Steinbrenner, Neustadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 189 days.

(21) Appl. No.: 10/450,117

(22) PCT Filed: Dec. 13, 2000

(86) PCT No.: PCT/EP01/14686

§ 371 (c)(1), (2), (4) Date: Jun. 11, 2003

(87) PCT Pub. No.: WO02/47813

PCT Pub. Date: Jun. 20, 2002

(65) Prior Publication Data

US 2004/0059168 A1 Mar. 25, 2004

(30) Foreign Application Priority Data

Dec. 14, 2000 (DE) ............... 100 62 242

(51) Int. Cl.
- B01J 21/18 (2006.01)
- B01J 23/02 (2006.01)
- C07C 2/04 (2006.01)
- C07C 2/24 (2006.01)
- C01B 31/24 (2006.01)

(52) U.S. Cl. ............ 502/174; 502/344; 585/510; 585/516; 423/419.1; 423/421

(58) Field of Classification Search ........ 502/174, 502/344; 423/419.1, 421; 585/510, 516
See application file for complete search history.

(56) References Cited

U.S. PATENT DOCUMENTS

| | | | |
|---|---|---|---|
| 3,389,190 A * | 6/1968 | Arthur et al. | 585/511 |
| 3,424,814 A * | 1/1969 | Grebbell et al. | 585/511 |
| 3,622,648 A * | 11/1971 | Schloemer et al. | 585/511 |
| 3,689,587 A * | 9/1972 | Grebball et al. | 585/329 |
| 4,179,580 A * | 12/1979 | Cobb | 546/349 |
| 4,544,790 A * | 10/1985 | Drake | 585/516 |
| 4,914,251 A * | 4/1990 | Knuuttila et al. | 585/453 |
| 4,916,100 A | 4/1990 | Knuuttila et al. | 502/174 |
| 4,952,546 A * | 8/1990 | Knuuttila et al. | 502/174 |
| 4,977,124 A * | 12/1990 | Smith | 502/174 |
| 5,105,049 A * | 4/1992 | Hasselbring | 585/516 |
| 5,132,483 A * | 7/1992 | Schubert | 585/511 |
| 5,202,298 A * | 4/1993 | Schubert et al. | 502/174 |
| 5,243,119 A * | 9/1993 | Smith | 585/516 |
| 5,329,058 A * | 7/1994 | Shimada et al. | 585/452 |
| 5,474,963 A * | 12/1995 | Nakagawa et al. | 502/184 |
| 6,043,189 A * | 3/2000 | Narbeshuber et al. | 502/344 |
| 6,284,704 B1 * | 9/2001 | Steinbrenner et al. | 502/344 |
| 6,414,207 B1 * | 7/2002 | Steinbrenner et al. | 585/452 |

FOREIGN PATENT DOCUMENTS

| | | |
|---|---|---|
| EP | 173 335 | 3/1986 |
| EP | 313 050 | 4/1989 |
| EP | 374315 * | 6/1990 |
| EP | 489 438 | 6/1992 |
| EP | 547 336 | 6/1993 |
| GB | 933 253 | 8/1963 |
| GB | 1269280 * | 4/1972 |
| GB | 2 249 737 | 5/1992 |
| GB | 2 254 802 | 10/1992 |
| GB | 2 276 833 | 10/1994 |
| WO | 88/04955 | 7/1988 |
| WO | 91/162841 | 10/1991 |

OTHER PUBLICATIONS

Derwent Abst. J 6 1053-229, no month/year.
Derwent Abst. J 6 1221-133, no month/year.
Derwent Abst. J 6 1227 536, no month/year.

* cited by examiner

Primary Examiner—J. A. Lorengo
Assistant Examiner—Patricia L. Hailey
(74) Attorney, Agent, or Firm—Novak Druce & Quigg, LLP

(57) ABSTRACT

The invention relates to a process for the preparation of an alkali metal catalyst by mixing an alkali metal with pulverulent, solid potassium carbonate as support, wherein the potassium carbonate has a specific surface area of at least 0.3 $m^2/g$, and to the use thereof for the side-chain alkylation of alkylbenzenes.

14 Claims, No Drawings

METHOD FOR PRODUCING ALKALI METAL CATALYST AND USE THEREOF FOR THE SIDE-CHAIN ALKLATION OF ALKYL AROMATICS

Process for the preparation of an alkali metal catalyst, and the use thereof for the side-chain alkylation of alkylaromatic compounds.

The present invention relates to a process for the preparation of an alkali metal catalyst, and to the use thereof for the side-chain alkylation of alkylaromatic compounds which have at least one alkyl side chain containing an a-hydrogen atom.

It is known that alkali metals catalyze the coupling of alkylaromatic compounds which have an active hydrogen atom on the α-carbon atom of the alkyl chain (benzylic hydrogen atom=α-hydrogen atom) with olefins. This process is also known as side-chain alkylation. The alkali metals employed are frequently sodium, potassium or sodium/potassium alloy. Owing to the comparatively low selectivity of the alkali metal for this reaction, however, by-products are frequently formed. Besides the formation of isomeric alkylaromatic compounds, which can frequently only be separated off from the desired target compound with difficulty, cyclization of the alkylaromatic compound formed primarily is also observed. Thus, for example, in the reaction of toluene with propene in the presence of alkali metals, n-butylbenzene and methylindanes are also found in addition to the desired isobutylbenzene. The low catalytic activity of the alkali metal catalysts, with the consequence of low space-time yields, is also problematic.

Various alkali metal catalysts for side-chain alkylation which comprise the alkali metal in finely divided form on an inorganic support have been described in the prior art. Supports which have proven particularly successful here are potassium carbonate (see, for example, GB 933,253, GB 2,249,737, GB 2,254,802, FR 2,609,024, EP-A 173 335, WO 88/04955, J 61053-229-A, J 61221-133-A and J 61227536-A) and mixtures of potassium carbonate with other potassium salts (see WO 91/16282 and the earlier German patent application P 10023771.1).

In particular, the space-time yields achieved with these catalysts are frequently inadequate. The selectivity is also not always satisfactory. In addition, the problem exists in the case of these catalysts that tar-like coatings deposit on the walls of the reactor, presumably attributable to the formation of alkali metal salts of acidic hydrocarbons, for example indenes, cyclopentadienes, dihydroanthracenes or 1-alkynes, or to polymerization processes.

It is an object of the present invention to provide an alkali metal catalyst which is suitable for the side-chain alkylation of alkylaromatic compounds using olefins. The catalyst should be distinguished by a good space-time yield and high selectivity.

We have found that this object is achieved, surprisingly, by an alkali metal catalyst in the form of an alkali metal finely distributed on an inorganic support material, where the inorganic material is a potassium carbonate having a specific surface area of at least 0.3 $m^2/g$.

The present invention thus relates firstly to a process for the preparation of an alkali metal catalyst by mixing an alkali metal with pulverulent, solid potassium carbonate as support, wherein the potassium carbonate has a specific surface area of at least 0.3 $m^2/g$. The invention also relates to the catalysts obtainable by this process.

During the preparation of the catalyst, chemical reactions of the support material potassium carbonate with the alkali metal may occur, resulting in a chemical change to the support. The present invention naturally also relates to these cases.

The advantageous properties of the catalysts according to the invention, such as selectivity and space-time yield, are due to the combination of potassium carbonate and the high specific surface area of the potassium carbonate. This is, in accordance with the invention, at least 0.3 $m^2/g$, preferably at least 0.32 $m^2/g$ and in particular at least 0.35 $m^2/g$, and is particularly preferably in the range from 0.35 to 3.0 $m^2/g$. The specific surface area in accordance with the invention is based on the so-called BET surface area, as determined in accordance with DIN 66131.

In the process according to the invention, a potassium carbonate having a larger specific surface area over a longer period results in significantly higher space-time yields and selectivities with respect to the target product. The crucial aspect is that the surface is a potassium carbonate surface. A high surface area of the support material per se is not sufficient to provide the advantages of the process according to the invention. Thus, for example, the addition of relatively large amounts of perovskite of high specific surface area, for example in the range from 10 to 20 $m^2/g$, to the support according to the invention does not produce any advantages, but instead significant disadvantages regarding the selectivity with respect to undesired ring closure reactions and shorter catalyst service lives. This effect is also found in the case of other inorganic supports of high specific surface area, such as aluminum oxide or magnesium oxide. Addition of other inorganic support materials of comparably high specific surface area can therefore only be tolerated in small amounts, for example in amounts of <10% by weight, in particular <5% by weight, based on the total amount of support material.

The origin of the potassium carbonate is of secondary importance for the process according to the invention so long as it has the surface area according to the invention. For example, the potassium carbonate may have been prepared from another potassium compound by heating, for example in air, carbon dioxide, oxygen or inert gas. The support employed is preferably a potassium carbonate which has preferably been prepared by carbonization of potassium hydroxide solution.

Sodium has proven particularly successful as alkali metal and in addition is inexpensive and easy to handle. It may comprise up to 5% by weight of other metals as are usually found in technical-grade sodium, for example potassium, calcium or strontium. In particular, use is made of technical-grade sodium, which usually contains less than 1% by weight of the above-mentioned metals as impurities.

In the alkali metal catalysts used in accordance with the invention, the weight ratio between the alkali metal and the potassium carbonate is preferably in the range from 1:1 to 1:50, in particular in the range from 1:2 to 1:30 and particularly preferably in the range from 1:5 to 1:20.

The catalysts according to the invention can be prepared in the ways that are known for the preparation of supported alkali metal catalysts. Mention may be made here of the following:

mixing of the molten alkali metal with the support material potassium carbonate, vapor deposition of the alkali metal onto the support material potassium carbonate, or impregnation of the support material potassium carbonate with the solution of the alkali metal in ammonia and removal of the ammonia.

In general, the potassium carbonate will contain only small amounts of water, preferably not more than 2000 ppm and in particular not more than 500 ppm. For this purpose, the potassium carbonate is subjected to a drying process before the treatment with the alkali metal. It is preferably warmed to temperatures of ≧100° C., in particular above 200° C. In order to support the drying, a reduced pressure can be applied and/or a stream of inert gas passed through the potassium carbonate.

It has furthermore proven favorable for the potassium carbonate used for the preparation of the alkali metal catalyst to have a mean particle size of less than 1000 μm, in particular less than 200 μm and particularly preferably in the range from 10 to 100 μm. In general, the potassium carbonate is ground in the apparatuses which are usual for this purpose, such as ball mills, Retsch mills or impact mills.

With respect to the process according to the invention, it has proven particularly favorable to employ an alkali metal catalyst which is obtainable by mixing the molten alkali metal at temperatures above the melting point of the alkali metal with the solid potassium carbonate in powder form. In particular, use is made here of a potassium carbonate which has been dried at temperatures of ≧200° C., for example from 250° C. to 400° C., in a stream of inert gas. The mixing is preferably carried out at a temperature of at least 100° C., preferably at least 150° C. and in particular at least 200° C. It is preferred here that a temperature of 500° C. and in particular 400° C. is not exceeded. In order to achieve good supporting, the mixing lasts at least 30 minutes, preferably at least 60 minutes and in particular at least 90 minutes.

For the mixing of the alkali metal with the support, the alkali metal can, for example, be added to the support in the form of an extrudate or block and mixed therewith with warming. It is of course also possible to add the pulverulent potassium carbonate to a melt of the alkali metal. The alkali metal is mixed with the support material in the apparatuses which are usual for this purpose, for example in stirred reactors, paddle dryers, compounders, pan mills or Discotherm apparatuses.

The mixing of alkali metal and inorganic substance is of course carried out under inert conditions, for example under an inert gas, such as nitrogen or argon, or under an inert-gas mixture, where the inert gas generally contains less than 500 ppm of oxygen and less than 100 ppm of water.

If desired, the alkali metal catalyst can, after application of the alkali metal to the support material, be hydrogenated by treating the mixture of alkali metal and support material with hydrogen or a mixture of an inert gas and hydrogen at temperatures in the range from 100° C. to 400° C., preferably in the range from 200° C. to 300° C. The catalyst is cooled and stored under inert gas.

In general, the hydrogenation is carried out at atmospheric pressure. The hydrogenation presumably causes the formation of alkali metal hydride catalysts, which likewise catalyze the basic side-chain alkylation. Without being bound to theory, it is assumed that partial hydrogenation of the catalyst by the hydrogen formed as by-product during the side-chain alkylation occurs in situ under the reaction conditions even without external supply of hydrogen.

In the presence of the catalyst according to the invention, reactions of alkylaromatic compounds containing α-hydrogen atoms with olefins can be carried out with high selectivity and good space-time yields. In addition, the catalysts according to the invention are suitable for carrying out dimerizations and co-dimerizations of olefins in a targeted manner.

Suitable olefins for the side-chain alkylation process according to the invention are monoolefins and conjugated olefins.

Suitable monoolefins for the side-chain alkylation are, in particular, those having from 2 to 10 and particularly preferably those having from 2 to 5 carbon atoms. Examples thereof are ethene, propene, 1-butene, 2-butene, isobutene, 1-pentene, 2-pentene, 2-methyl-1-butene, 2-methyl-2-butene and 3-methyl-1-butene. Particularly preferably monoolefins are ethene, propene and 1- or 2-butenes.

The catalysts according to the invention may in addition be used for the dimerization of the above-mentioned olefins, for example for the dimerization of propene to hexene or preferably for the co-dimerization of ethene with 1- or 2-butene to give hexenes.

Suitable conjugated diolefins for the side-chain alkylation of alkylaromatic compounds are those having from 4 to 10 carbon atoms, such as 1,3-butadiene, 2-methyl-1,3-butadiene, 1,3-pentadiene, etc., in particular 1,3-butadiene.

The alkylaromatic compounds employed are generally derivatives of benzene or of naphthalene which contain one, two or three alkyl radicals having from 1 to 10 carbon atoms, preferably having from 1 to 6 carbon atoms and in particular having from 1 to 3 carbon atoms, where at least one of these radicals has a hydrogen atom on an a-carbon atom. Typical alkyl radicals are methyl, ethyl, n-propyl, isopropyl, n-butyl, 2-butyl, isobutyl and n-pentyl. Examples of compounds of this type are mono-, di- and tri-$C_1$-$C_3$-alkylbenzenes, such as toluene, xylenes, methylnaphthalenes, mesitylene, ethylbenzenes and isopropylbenzenes, where the two last-mentioned types of compound may also contain one or two further methyl groups. Likewise suitable are derivatives of benzene or of naphthalene in which two alkyl radicals, together with the aromatic ring to which they are bonded, form an alicyclic ring, which may also contain an oxygen atom. Examples of compounds of this type are 1,2,3,4-tetrahydronaphthalene, indanes and chromane. Preferred alkylaromatic compounds are derivatives of benzene, in particular those which have one or two alkyl groups. Preferred alkylaromatic compounds have, in particular, at least one methyl group and/or isopropyl group. Examples of preferred alkylaromatic compounds are toluene, ortho-xylene, meta-xylene, para-xylene, 1-ethyl-2-methylbenzene, 1-ethyl-3-methylbenzene, 1,2,4-trimethylbenzene, isopropylbenzene and 4-isopropyl-1-methylbenzene.

Of the said alkylaromatic compounds, toluene, xylenes and isopropylbenzene are particularly preferred, and toluene and o-xylene are very particularly preferred. The process according to the invention can be employed, for example, for the reaction of cumene with ethene to give tert-amylbenzene, of toluene with ethene to give n-propylbenzene, for the reaction of xylenes with 1- or 2-butene to give the corresponding tolylpentanes or for the reaction of xylenes with 1,3-butadiene to give tolylpentenes, and particularly preferably for the reaction of toluene with propene to give isobutylbenzene and for the reaction of o-xylene with 1,3-butadiene to give o-tolylpentenes.

The alkylation is generally carried out at elevated temperature, i.e. at temperatures above room temperature, preferably above 80° C. and in particular above 100° C. In general, the reaction temperature in the process according to the invention will not exceed 300° C., preferably 250° C. and in particular 200° C. The reaction is particularly preferably carried out below 180° C. and very particularly preferably below 160° C., for example at from 120° C. to 140° C.

The process according to the invention can be carried out either in the gas phase or in the liquid phase. The olefin can also be passed in gaseous form into the liquid reaction phase comprising the alkali metal catalyst and the alkylaromatic compound. The reaction is preferably carried out in a liquid reaction phase. Besides the starting materials, the liquid reaction phase may also comprise a solvent which is inert under the reaction conditions. Examples thereof are aliphatic and alicyclic hydrocarbons, such as octane, hexane, cyclohexane, cyclooctane and decalin. However, the process is preferably carried out without a solvent, i.e. the liquid reaction phase comprises only the liquid starting components and the alkali metal catalyst.

In general, the process will be carried out with exclusion of traces of oxygen and water. The starting materials generally contain less than 1000 ppm and very particularly preferably less than 100 ppm of water. The oxygen content of the starting materials is generally less than 500 ppm and particularly preferably less than 50 ppm. In general, the water is to this end separated off from the starting materials by known methods, for example by using desiccants, such as active aluminum oxide, silica gel, molecular sieve or activated carbon, by treatment with metallic sodium or potassium or by freezing out.

If the reaction is carried out in the liquid phase, the reaction can be carried out either under an inert-gas atmosphere or under the inherent vapor pressure of the liquid reaction phase. However, the reaction is preferably carried out in a completely or virtually completely flooded reactor which contains virtually no gas phase any longer. This procedure is particularly preferred if the process is carried out continuously.

In the process according to the invention, the olefin is preferably employed in a sub-stoichiometric molar amount, based on the alkylaromatic compound. The molar ratio between the olefin and the alkylaromatic compound will preferably not exceed a value of 0.8, in particular 0.6 and particularly preferably 0.5. However, the molar ratio will preferably be at least 0.1, in particular 0.2 and particularly preferably at least 0.3. Through this measure, the dimerization of the olefin and subsequent reactions of the alkylaromatic compound formed in the reaction, which may still have active a-hydrogen atoms, are prevented. It is also possible to employ an excess of olefin, based on the alkylaromatic compound, in the process according to the invention, in particular if an alkylaromatic compound which contains no a-hydrogen atom is formed in the process according to the invention, for example the tert-amylbenzene formed in the reaction of cumene with ethene.

The process according to the invention can be designed as a batch process or as a continuous process.

In the batch method, a procedure is generally followed in which the alkylaromatic compound and the alkali metal catalyst are initially introduced, and the olefin, preferably in liquid form, is added thereto under the reaction conditions to the extent that it is consumed. In this way, it is achieved that the olefin is present in the reaction mixture in a sub-stoichiometric amount, based on the alkylaromatic compound. When the desired conversion has been reached, the reaction is terminated by cooling the reaction mixture, the alkali metal catalyst is separated off, and the product is worked up in the conventional manner for this purpose, preferably by distillation.

The process according to the invention is preferably carried out continuously. For this purpose, the starting materials are passed continuously through a reaction zone charged with the catalyst under the reaction conditions. The alkali metal catalyst may be present in the reaction zone in the form of a fixed bed. Preferably, however, it is present in the form of a suspension in the liquid reaction phase. For this purpose, the liquid reaction phase is preferably stirred vigorously, for example using impeller turbines or using anchor stirrers.

In the continuous embodiment of the process according to the invention, the starting materials can be fed into the reactor in a single stream or in separate streams. The rate at which the starting materials are fed into the reactor (feed rate) naturally depends on the reactivity of the starting materials and of the catalyst. The feed rate is preferably in the range from 0.05 to 5 kg of starting materials per kilogram of catalyst material and per hour, in particular in the range from 0.1 to 1 kg/h per kilogram of catalyst material. In the case of continuous feed of the starting materials, a molar ratio between the alkylaromatic compound and the olefin of less than 1 and in particular in the range from 1:10 to 1:2 and especially in the range from 1:4 to 2:3 is preferably selected.

In order to isolate the target product from the liquid reaction phase, the catalyst is generally separated off from the reaction phase, and the latter is worked up by distillation. Residues of catalyst remaining in the reaction phase owing to incomplete catalyst removal are generally deactivated before the work-up, for example by addition of water and/or alkanols, such as methanol, ethanol or isopropanol. In the case of a continuous reaction, a procedure is generally followed in which an amount of liquid reaction phase corresponding to the amount fed in is discharged from the reactor and worked up in the manner described above. The discharge of the liquid reaction phase is preferably carried out with substantial or complete retention of the alkali metal catalyst in the reaction space. The catalyst is retained, for example, by means of suitable filters or separators, such as cross-flow filters, cartridge filters, membranes or settlers.

In the subsequent distillative work-up, the liquid reaction phase is separated into the valuable product, by-products, any solvent and excess alkylaromatic compound. Any excess alkylaromatic compound obtained is preferably fed back into the process.

The dimerization and co-dimerization of olefins is preferably carried out analogously to the side-chain alkylation of alkylaromatic compounds.

The alkali metal catalysts according to the invention give the alkylaromatic compounds desired in each case in high selectivity and space-time yield. Surprisingly, the alkali metal catalysts which are suitable in accordance with the invention are superior to the alkali metal catalysts from the prior art with respect to the service life.

The following examples serve to illustrate the invention.

I. Preparation of the Catalysts

1. General Preparation Procedure 70 g of potassium carbonate were ground and dried at 300° C. for 15 hours with stirring in a Duran glass vessel in a stream of argon. After cooling, 10.8 g of metallic sodium (technical grade) were added, and the mixture was re-heated at 300° C. for 2 hours with stirring in a stream of argon. After cooling, the resultant solid was suspended in 75 g of absolute toluene under argon with stirring. In this way, a catalyst suspension was obtained.

2. The following catalysts were prepared and tested:

Catalyst A: 10.8 g of sodium on 70 g of potassium carbonate, BET surface area of the potassium carbonate (measured in accordance with DIN 66131)=0.39 $m^2/g$ (according to the invention).

Catalyst B: 10.8 g of sodium on a mixture of 70 g of dry CaTiO$_3$ (BET surface area 14.6 m$^2$/g) and 70 g of potassium carbonate (not according to the invention).

Catalyst C: 10.8 g of sodium on 70 g of potassium carbonate having a BET surface area of 0.29 m$^2$/g (not according to the invention).

II. Reaction of Toluene with Propene

1. General Procedure

The reaction was carried out continuously in a stirred-tank reactor having an internal capacity of 270 ml which was fitted with a magnetically coupled stirrer with impeller turbine. The reactor in each case contained the catalyst suspension and was flooded with the mixture of liquid propene and toluene before commencement of the reaction. The reactor was warmed to 130° C. and stirred at speeds in the range from 1000 to 1200 rpm. 0.132 mol/h of dry liquid propene and 0.316 mol/h of dry toluene were fed continuously into the reactor. The reaction product was discharged via a 4 mm filter and analyzed for the contents of the products by on-line gas chromatography.

Tables 1 to 3 below show the results for run times in the range from 10 to 100 hours.

2. EXAMPLE 1

Reaction with Catalyst A in Accordance with the General Procedure

| Run time | | Selectivity[2] [mol %] | | | |
|---|---|---|---|---|---|
| [h] | STY[1] | T → IBB | T → nBB | T → I | P → IBB |
| 10 | 0.036 | 87 | 10.8 | 0.8 | 71 |
| 20 | 0.085 | 87 | 10.2 | 1.0 | 78 |
| 30 | 0.096 | 87 | 9.7 | 1.1 | 78 |
| 40 | 0.093 | 87 | 9.4 | 1.2 | 78 |
| 50 | 0.090 | 88 | 8.9 | 1.3 | 78 |
| 60 | 0.086 | 88 | 8.6 | 1.5 | 78 |
| 70 | 0.081 | 88 | 8.0 | 1.9 | 78 |
| 80 | 0.078 | 88 | 7.4 | 2.2 | 79 |
| 90 | 0.076 | 89 | 6.9 | 2.6 | 79 |
| 100 | 0.074 | 89 | 6.3 | 2.9 | 79 |

T = toluene, IBB = isobutylbenzene, nBB = n-butylbenzene, I = indane, P = propene, cat = catalyst, GC = gas chromatogram
[1]STY = space-time yield in g of (IBB)/(g of (cat) ○h).
[2]Selectivity calculated from the GC peak area %, on the basis that the relative peak area corresponds to the proportion in % by weight.

| Run time | | Selectivity[2] [mol %] | | | |
|---|---|---|---|---|---|
| [h] | STY[1] | T → IBB | T → nBB | T → I | P → IBB |
| 10 | 0.047 | 82 | 2.8 | 9.8 | 75 |
| 20 | 0.073 | 82 | 2.6 | 14.7 | 73 |
| 30 | 0.070 | 82 | 2.5 | 16.6 | 72 |
| 40 | 0.069 | 81 | 2.4 | 16.6 | 72 |
| 50 | 0.067 | 81 | 2.4 | 16.7 | 70 |
| 60 | 0.062 | 81 | 2.4 | 16.7 | 71 |
| 70 | 0.058 | 81 | 2.3 | 16.6 | 71 |
| 80 | 0.058 | 81 | 2.3 | 16.7 | 71 |
| 90 | 0.056 | 81 | 2.3 | 16.7 | 70 |
| 100 | 0.054 | 81 | 2.3 | 16.7 | 70 |

T = toluene, IBB = isobutylbenzene, nBB = n-butylbenzene, I = indane, P = propene, cat = catalyst, GC = gas chromatogram
[1]STY = space-time yield in g of (IBB)/(g of (cat) ○h). For reasons of comparability, it is only calculated with respect to the amounts of NaCO$_3$ and K$_2$CO$_3$.
[2]Selectivity calculated from the GC peak area %, on the basis that the relative peak area corresponds to the proportion in % by weight.

3. COMPARATIVE EXAMPLE 2

Reaction with Catalyst C in Accordance with the General Procedure

| Run time | | Selectivity[2] [mol %] | | | |
|---|---|---|---|---|---|
| [h] | STY[1] | T → IBB | T → nBB | T → I | P → IBB |
| 10 | 0.016 | 88 | 10.2 | 0.6 | 30 |
| 20 | 0.079 | 88 | 10.6 | 0.6 | 75 |
| 30 | 0.088 | 88 | 10.6 | 0.6 | 77 |
| 40 | 0.091 | 88 | 10.4 | 0.7 | 78 |
| 50 | 0.084 | 88 | 10.0 | 0.8 | 78 |
| 60 | 0.074 | 88 | 9.6 | 0.9 | 76 |
| 70 | 0.070 | 89 | 9.3 | 1.1 | 76 |
| 80 | 0.063 | 89 | 8.8 | 1.3 | 76 |
| 90 | 0.050 | 89 | 8.4 | 1.6 | 76 |
| 100 | 0.046 | 89 | 8.1 | 1.7 | 76 |

T = toluene, IBB = isobutylbenzene, nBB = n-butylbenzene, I = indane, P = propene, cat = catalyst, GC = gas chromatogram
[1]STY = space-time yield in g of (IBB)/(g of (cat) ○h).
[2]Selectivity calculated from the GC peak area %, on the basis that the relative peak area corresponds to the proportion in % by weight.

The results show that the catalysts according to the invention are superior to the catalysts comprising conventional potassium carbonate as support with respect to the selectivity-of isobutylbenzene vs. n-butylbenzene. Although a lower isobutylbenzene vs. n-butylbenzene selectivity is observed compared with perovskite-containing catalysts, this is, however, outweighed by on average lower selectivities of the perovskite catalysts with respect to the disadvantageous formation of methylindane. Surprisingly, the catalysts according to the invention are distinguished by better space-time yields, in particular with longer service lives.

I claim:

1. A process for the preparation of an alkali metal catalyst by mixing an alkali metal with an inorganic support material which consists of pulverulent, solid potassium carbonate and up to 10% by weight of inorganic support material different therefrom, wherein the potassium carbonate has a specific surface area of at least 0.3 m$^2$/g.

2. A process as claimed in claim 1, wherein the alkali metal is sodium.

3. A process as claimed in claim 1, wherein the weight ratio between the alkali metal and the potassium carbonate in the catalyst is in the range from 1:1 to 1:50.

4. A process as claimed in claim 1, wherein use is made of a potassium carbonate which is dried in a stream of inert gas at temperatures ≧100° C.

5. A process as claimed in claim 1, wherein the mixing of the alkali metal with the pulverulent, solid potassium carbonate is carried out at above the melting point of the alkali metal.

6. A process as claimed in claim 5, wherein the mixing is carried out at a temperature above 100° C.

7. A process as claimed in claim 1, wherein the catalyst is treated with hydrogen after the mixing.

8. An alkali metal catalyst obtained by the process claimed in claim 1.

9. A process for the side-chain alkylation of alkylaromatic compounds having at least one alkyl side chain containing an α-hydrogen atom, which comprises reacting the alkylaromatic compound with an olefin in the presence of the catalyst as claimed in claim 8.

10. A process as claimed in claim 9, wherein the catalyst is in suspension during the reaction.

11. A process as claimed in claim 9, wherein the alkylaromatic compound is a derivative of benzene or naphthalene which has one, two or three alkyl radicals having from 1 to 10 carbon atoms.

12. A process as claimed in claim 9, wherein the olefin is a monoolefin.

13. A process as claimed in claim 12, wherein the catalyst is in suspension during the reaction.

14. A process for the dimerization and co-dimerization of monoolefins, which comprises dimerizing the monoolefins in the presence of the catalyst as claimed in claim 8.

* * * * *

UNITED STATES PATENT AND TRADEMARK OFFICE
CERTIFICATE OF CORRECTION

| | |
|---|---|
| PATENT NO. | : 7,148,177 B2 |
| APPLICATION NO. | : 10/450117 |
| DATED | : December 12, 2006 |
| INVENTOR(S) | : Steinbrenner |

It is certified that error appears in the above-identified patent and that said Letters Patent is hereby corrected as shown below:

On the title page item (22) the PCT Filing date
    "December 13, 2000" should read -- December 13, 2001 --

Claim 8, col. 9, indicated lines 9 and 10:
    "the process claimed in claim 1." should read
    -- mixing an alkali metal with an inorganic support material which consists of pulverulent, solid potassium carbonate and up to 10% by weight of inorganic support material different therefrom, wherein the potassium carbonate has a specific surface area of at least 0.3 $m^2/g$. --

Signed and Sealed this

Tenth Day of April, 2007

JON W. DUDAS
*Director of the United States Patent and Trademark Office*